United States Patent
Heider et al.

[11] Patent Number: 5,723,685
[45] Date of Patent: Mar. 3, 1998

[54] PREPARATION OF MONOVINYL ETHERS

[75] Inventors: Marc Heider, Neustadt; Thomas Rühl; Herbert Helfert, both of Frankenthal; Martin Schmidt-Radde, Beindersheim; Jochem Henkelmann, Mannheim, all of Germany

[73] Assignee: BASF Aktiengesellschaft, Ludwigshafen, Germany

[21] Appl. No.: 548,739

[22] Filed: Oct. 26, 1995

[30] Foreign Application Priority Data

Oct. 19, 1994 [DE] Germany ............... 44 38 707.5

[51] Int. Cl.$^6$ ............................................. C07C 41/00
[52] U.S. Cl. ............................................. 568/688; 568/687
[58] Field of Search ............................................. 568/608

[56] References Cited

U.S. PATENT DOCUMENTS

| | | | |
|---|---|---|---|
| 1,959,927 | 5/1934 | Reppe et al. | 260/127 |
| 3,657,360 | 4/1972 | Carluccio et al. | 260/615 |

FOREIGN PATENT DOCUMENTS

| | | |
|---|---|---|
| 1159861 | 7/1958 | France . |
| 958 383 | 1/1957 | Germany . |
| 26 28 408 | 1/1978 | Germany . |
| 773 331 | 4/1957 | United Kingdom . |
| 773331 | 4/1957 | United Kingdom . |

OTHER PUBLICATIONS

Reppe et al. (Liebigs Ann. Chem. 601 (1956) 81 Synthesis of Some Derivatives. . ., Mikant'ev et al. Plenum Pub. Corp. 1990, 157–161.

*Chem. Abst.*, vol. 48, No. 2, Jan. 25, 1954, Shostakovskii et al., vol. 586g.

*Primary Examiner*—Raymond Henley, III
*Assistant Examiner*—Dwayne C. Jones
*Attorney, Agent, or Firm*—Kiel & Weinkauf

[57] ABSTRACT

The preparation of monovinyl ethers of the general formula I

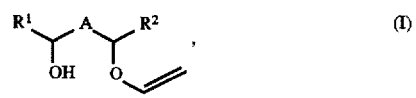

in which A stands for a chemical bond or for a methylene or ethylene group, the radicals $R^1$ and $R^2$ independently stand for hydrogen, alkyl, cycloalkyl, or aryl groups or $R^1$ and $R^2$ together form a $C_3$–$C_5$ alkylene bridging member, by the reaction of a diol of the general formula II

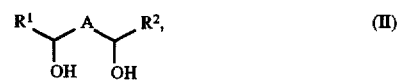

in which the variables have the above meanings, with acetylene in the presence of a base, in which the reaction is carried out at 150°–250° C. under an acetylene partial pressure of 5–25 bar until 40–80% of the diol has been converted, at which point the reaction is stopped and the monovinyl ether of the formula I is isolated.

6 Claims, No Drawings

PREPARATION OF MONOVINYL ETHERS

BACKGROUND OF THE INVENTION

1. Field of the Invention

The present invention relates to an improved process for the preparation of monovinyl ethers of the general formula I

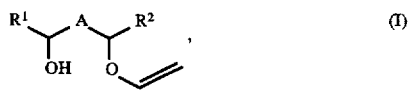

in which A stands for a chemical bond or for a methylene or ethylene group, the radicals $R^1$ and $R^2$ independently stand for hydrogen, alkyl, cycloalkyl, or aryl groups or $R^1$ and $R^2$ together form a $C_3$-$C_5$ alkylene bridging member, by the reaction of a diol of the general formula II

in which the variables have the above meanings, with acetylene in the presence of a base.

2. Description of the Related Art

Reppe et al (*Liebigs Ann. Chem.* 601 (1956) 81) disclose that the reaction of diols of the formula II with acetylene leads to mixtures of the corresponding monovinyl ethers, the divinyl ethers (by double reaction of the hydroxyl groups with acetylene) and of cyclic acetals. The acetals are formed in particular from the monovinyl ethers of 1,2-diols with the formation of five-membered rings.

The reference teaches the vinylation of ethylene glycol at 120° C. and 20 bar of acetylene pressure. The space-time yield of 15.8 g of monovinylether/L·h is unsatisfactory for large-scale use. At a reaction temperature of 180° C., the unwanted cyclic glycol acetal formed the main product of the reaction.

DE-A 958,383 relates to the preparation of monovinyl ethers of diols at reaction temperatures above 180° C. under standard pressure conditions. In this process the monovinyl ether formed is driven out of the reaction mixture by passing in acetylene in excess and is then isolated. This mode of operation requires the use of a considerable excess of acetylene. To effect economical operation of an appropriate plant the acetylene must be purified following isolation of monovinyl ether and recycled to the reaction. Such a procedure involves elaborate engineering means and is thus undesirable.

Mikhanteo et al (*Zh. Prikl. Khim.* 63 (1990) 172) describe the vinylation of diols at 145° C. and 1 bar of pressure. The monovinyl ethers are referred to as being unstable under the reaction conditions; they continue to react to form the divinyl ethers or the corresponding cyclic acetals.

It was the object of the present invention to provide a process which makes possible the preparation of monovinyl ethers to a high degree of selectivity. The proportion of cyclic by-products formed should be small. It was a particular object of the present invention to provide a process which produces a high space-time yield.

SUMMARY OF THE INVENTION

Accordingly, we have found the process defined above for the preparation of monovinyl ethers of the formula I, wherein the reaction is carried out at 150°–250° C. under an acetylene partial pressure of 5–25 bar until 40–80% of the diol has been converted, at which point the reaction is stopped and the monovinyl ether of the formula I is isolated.

Suitable starting materials for the process are diols of the formula II. The variable A therein can stand for a chemical bond or a methylene or ethylene group.

DESCRIPTION OF THE PREFERRED EMBODIMENTS

The radicals $R^1$ and $R^2$ independently stand for hydrogen, alkyl groups, preferably $C_1$-$C_6$ alkyl such as methyl, ethyl, and n-propyl, and also cyoloalkyl groups, preferably $C_4$-$C_7$ cycloalkyl such as cyclopentyl and cyclohexyl, or an aryl group, $C_6$-$C_{10}$ aryl such as phenyl being preferred. The aryl groups can carry one to three inert substituents such as alkyl, alkoxy, or halogen radicals. Alternatively, the radicals $R^1$ and $R^2$ can together form a $C_3$-$C_5$ alkylene group.

Suitable diols of the formula II are: ethylene glycol, 1,2-propylene glycol, 1,3-propylene glycol, 1,2-butanediol, 1,3-butanediol, 1,4-butanediol, 2,5-hexanediol, 2,3-hexanediol, and 1,2-cyclohexanediol. Ethylene glycol, 1,2-propylene glycol, and 1,4-butanediol are preferred.

These diols are commercially available or can be prepared in known manner from the corresponding epoxides by decyclization by means of alkali metal hydroxides.

Acetylene can be used undiluted or diluted with inert gases such as nitrogen, methane, propane, or argon. Acetylene is generally used in amounts of from 0.4 to 5 mol per mole of diol.

Suitable bases are theoretically all compounds which are capable of forming the corresponding monoalcoholate from the diols of the formula II.

Specifically, the following classes of compounds may be mentioned:

alkali metal hydrides such as NaH and KH;

alkali metal amides such as sodium amide and potassium amide;

alkali metal hydroxides and alkaline earth metal hydroxides such as NaOH, KOH, CsOH and Ca(OH)$_2$;

alkali metal alcoholates such as sodium methylate and potassium methylate.

Potassium hydroxide is preferred.

The bases can be used in catalytic amounts, 0.005–0.05 mol per mole of diol being usually sufficient.

In a preferred embodiment, the diol and potassium hydroxide are heated with evaporation of water to form the monopotassium salt of the diol. Acetylene is then added to this mixture.

The reaction can be carried out in an inert solvent such as THF or diethylene glycol dimethyl ether; preferably, however, no solvent is added.

The temperature of reaction is 150°–250° C., preferably 150°–180° C. There is increased formation of the undesirable acetal above this temperature, while below no satisfactory space-time yield can be achieved.

The acetylene partial pressure is 5–25 bar, preferably 10–20 bar. Below this range the reaction proceeds too slowly to achieve an acceptable reaction time. No appreciable advantage is to be gained from the use of higher pressures, which can be realized only by the use of elaborate means.

The reaction is stopped at a conversion of 40–80% of the diol. The degree of conversion can be readily determined, for example, by the removal of a sample and gas chromatographic analysis thereof.

Depending on the process conditions chosen, the reaction times are generally from 1 to 20 h.

The reaction can be carried out continuously or batchwise. Reactors such as stirred autoclaves or tubular reactors are suitable.

When a conversion of 40–80% of the diol has been reached, the reaction can be stopped by depressurizing the reaction mixture. The end product I is usually isolated from the effluent by distillation. Unconverted diol of the formula II can be recycled to the reaction following isolation thereof.

The present invention allows for the preparation of the monovinyl ethers I in high selectivity and in good space-time yields.

The end products I serve as intermediates for the manufacture of radiation-curable coating compositions. In addition, the divinyl ethers obtained as by-products can be employed as cross-linkable monomers for radiation-curable coating compositions.

EXAMPLES

Example 1

A mixture of 14 kg of ethylene glycol and 450 g of KOH, which had been previously distilled in vacuo for 2 h to remove 150 g of water, was placed in a high-pressure autoclave having a capacity of 20 L. Nitrogen was forced in to establish a pressure of 2 bar. The autoclave was heated to the temperature stated in Table 1. Acetylene was subsequently forced in to establish a total pressure of 20 bar. Consumed acetylene was replenished. On completion of the reaction, the effluent was cooled, depressurized, and distilled. Table 1 lists the results for various reaction temperatures (S stands for the selectivity toward the reaction product stated).

TABLE 1

| Temperature [°C.] | Time [h] | Conversion of Diol [%] | S (monovinyl ether) [%] | S (divinyl ether) [%] | S (acetal) [%] | Space-time Yield [g/l·h] |
|---|---|---|---|---|---|---|
| 130 (comparison) | 58 | 57 | 76 | 19 | 5 | 7.42 |
| 150 | 20 | 71 | 65 | 26 | 9 | 22.93 |
| 160 | 12 | 68 | 67 | 23 | 10 | 37.72 |
| 170 | 10 | 51 | 68 | 15 | 17 | 34.46 |

At 130° C. there was achieved only an unsatisfactory space-time yield.

Example 2

In a manner similar to that described in Example 1, 100 g of 1,2-propanediol and 5 g of KOH were caused to react in a high-pressure autoclave having a capacity of 300 mL. Table 2 lists the results.

TABLE 2

| Temperature [°C.] | Time [h] | Conversion of Diol [%] | S (monovinyl ether) [%] | S (divinyl ether) [%] | S (acetal) [%] | Space-time Yield [g/l·h] |
|---|---|---|---|---|---|---|
| 130 (comparison) | 62 | 66.8 | 78.1 | 12.5 | 9.4 | 3.37 |
| 150 | 6 | 80.6 | 75.4 | 13.3 | 11.3 | 40.5 |
| 160 | 3.5 | 67.4 | 77.4 | 12.2 | 10.4 | 59.6 |
| 170 | 3.5 | 73.1 | 58.2 | 12.3 | 29.5 | 48.6 |

Example 3

A tubular reactor having a capacity of 6 L was filled with ethylene glycol, in which 2.62 wt % of KOH had been dissolved with subsequent dehydration. At 160° C. and a pressure of 20 bar there were introduced into the reactor, per hour, 450 L of acetylene via a nozzle and 1.2 kg of ethylene glycol/KOH having the above composition via a high-pressure pump. The continuous overflow was depressurized and analyzed.

conversion: 60% selectivity (monovinyl ether): 59% selectivity (divinyl ether): 35% selectivity (acetal): 6% space-time yield (monovinyl ether): 70.8 g/l·h

We claim:

1. A process for the preparation of monovinyl ethers of the formula I $$R^1\underset{OH}{\diagdown}A\underset{O}{\diagup}R^2\diagdown\!\!\!=, \qquad (I)$$

in which A stands for a chemical bond or for a methylene or ethylene group, the radicals $R^1$ and $R^2$ independently stand for hydrogen, alkyl, cycloalkyl, or aryl groups or $R^1$ and $R^2$ together form a $C_3$–$C_5$ alkylene bridging member, which comprises: reacting a diol of the formula II $$R^1\underset{OH}{\diagdown}A\underset{OH}{\diagup}R^2, \qquad (II)$$

in which the variables have the above meanings, with acetylene in the presence of a base at 150°–250° C. under an acetylene partial pressure of 5–25 bar until 40–80% of the diol has been converted, at which point the reaction is stopped and the monovinyl ether of the formula I is isolated.

2. A process as defined in claim 1, which involves the conversion of ethylene glycol, 1,2-propylene glycol, or 1,4-butanediol.

3. A process as defined in claim 1, wherein the temperature of reaction is 150°–180° C.

4. A process as defined in any of claim 1, wherein the base is potassium hydroxide or a potassium alcoholate.

5. A process as defined in claim 2, wherein the temperature of reaction is 150°–180° C.

6. A process as defined in claim 5, wherein the base is potassium hydroxide or a potassium alcoholate.

* * * * *

UNITED STATES PATENT AND TRADEMARK OFFICE
CERTIFICATE OF CORRECTION

PATENT NO.: 5,723,685

DATED: March 3, 1998

INVENTOR(S): HEIDER et al.

It is certified that error appears in the above-identified patent and that said Letters Patent is hereby corrected as shown below:

On the cover page, item [30], the foreign application priority date
   "Oct. 19, 1994" should be --Oct. 29, 1994--.

On the cover page, the Attorney, Agent or Firm, "Kiel" should be --Keil--.

Signed and Sealed this

Twenty-sixth Day of May, 1998

Attest:

BRUCE LEHMAN

Attesting Officer      Commissioner of Patents and Trademarks